United States Patent
Ji et al.

(10) Patent No.: US 10,080,759 B2
(45) Date of Patent: Sep. 25, 2018

(54) METHODS OF TREATING PRURITUS

(71) Applicants: Duke University, Durham, NC (US); Biomimetix JV, LLC, Englewood, CO (US)

(72) Inventors: Ru-Rong Ji, Chapel Hill, NC (US); Tong Liu, Durham, NC (US); Ines Batinic-Haberle, Durham, NC (US); David S. Warner, Chapel Hill, NC (US); Kimberly C. Stone, Grenwood Village, CO (US); James D. Crapo, Englewood, CO (US)

(73) Assignees: Duke University, Durham, NC (US); BioMimetix J.V., LLC, Englewood, CO (US)

( * ) Notice: Subject to any disclaimer, the term of this patent is extended or adjusted under 35 U.S.C. 154(b) by 0 days.

(21) Appl. No.: 15/109,164

(22) PCT Filed: Jan. 21, 2015

(86) PCT No.: PCT/US2015/012228
§ 371 (c)(1),
(2) Date: Jun. 30, 2016

(87) PCT Pub. No.: WO2015/112586
PCT Pub. Date: Jul. 30, 2015

(65) Prior Publication Data
US 2016/0324868 A1    Nov. 10, 2016

Related U.S. Application Data
(60) Provisional application No. 61/930,132, filed on Jan. 22, 2014.

(51) Int. Cl.
*A61K 31/555*  (2006.01)
*A61K 31/4188*  (2006.01)
*A61K 9/00*  (2006.01)

(52) U.S. Cl.
CPC .......... *A61K 31/555* (2013.01); *A61K 9/0014* (2013.01); *A61K 9/0019* (2013.01); *A61K 31/4188* (2013.01)

(58) Field of Classification Search
CPC .. A61K 31/555; A61K 9/0014; A61K 9/0019; A61K 31/4188
USPC ........................................................ 514/188
See application file for complete search history.

(56) References Cited

U.S. PATENT DOCUMENTS

| | | |
|---|---|---|
| 3,936,385 A | 2/1976 | Cheng |
| 4,257,433 A | 3/1981 | Kwan |
| 4,865,545 A | 9/1989 | La Rocca |
| 5,061,106 A | 10/1991 | Kent |
| 5,141,290 A | 8/1992 | Mairon |
| 5,152,686 A | 10/1992 | Duggan et al. |
| 5,223,537 A | 6/1993 | Stjernschantz et al. |
| 5,785,523 A | 7/1998 | Overmyer |
| 5,939,051 A | 8/1999 | Santalucia et al. |
| 5,968,480 A | 10/1999 | Bergeron et al. |
| 5,989,526 A | 11/1999 | Aaslyng et al. |
| 6,270,890 B1 | 8/2001 | Curtis et al. |
| 6,289,904 B1 | 9/2001 | Suhonen et al. |
| 6,372,727 B1 * | 4/2002 | Crow ................... A61K 31/555 514/185 |
| 6,416,744 B1 | 7/2002 | Robinson et al. |
| 6,479,477 B1 | 11/2002 | Crapo et al. |
| 6,514,483 B2 | 2/2003 | Xu et al. |
| 6,583,132 B1 | 6/2003 | Crapo et al. |
| 6,592,849 B2 | 7/2003 | Robinson et al. |
| 6,680,299 B2 | 1/2004 | Or et al. |
| 6,680,322 B2 | 1/2004 | Castelhano et al. |
| 6,680,324 B2 | 1/2004 | Castelhano et al. |
| 6,844,004 B2 | 1/2005 | Andersson |
| 6,916,799 B2 | 7/2005 | Fridovich et al. |
| 7,025,950 B2 | 4/2006 | Majeti et al. |
| 7,229,286 B2 | 6/2007 | Jones et al. |
| 7,251,849 B2 | 8/2007 | Moskovich et al. |
| 7,264,005 B2 | 9/2007 | Wong |
| 7,297,327 B2 | 11/2007 | Pilch et al. |
| 7,531,186 B2 | 5/2009 | Boeckh et al. |
| 7,976,854 B2 | 7/2011 | Hattendorf et al. |
| 8,003,636 B2 | 8/2011 | Wollmann et al. |
| 8,183,364 B2 | 5/2012 | Batinic-Haberle et al. |
| 8,211,656 B2 | 7/2012 | Hyde et al. |
| 8,217,166 B2 | 7/2012 | Salvemini et al. |
| 8,470,808 B2 | 6/2013 | Piganelli et al. |
| 8,486,928 B2 | 7/2013 | Riley |
| 8,513,305 B2 | 8/2013 | Davies |
| 2001/0012856 A1 | 8/2001 | Parks et al. |
| 2003/0229065 A1 | 12/2003 | Levy et al. |
| 2004/0023941 A1 | 2/2004 | Crapo et al. |
| 2010/0267825 A1 | 10/2010 | Malfroy-Camine |

(Continued)

FOREIGN PATENT DOCUMENTS

| | | |
|---|---|---|
| WO | WO 97/35573 A2 | 10/1997 |
| WO | WO 00/43395 A1 | 7/2000 |
| WO | WO 2008/129000 A1 | 10/2008 |
| WO | WO 2013/071059 A1 | 5/2013 |

OTHER PUBLICATIONS

Batinic-Haberle et al. Free Radiacal Biology & Medicine (2011), vol. 51 pp. 1035-1053.*

(Continued)

*Primary Examiner* — Melenie L McCormick
*Assistant Examiner* — Taina D Matos Negron
(74) *Attorney, Agent, or Firm* — Myers Bigel, P.A.

(57) ABSTRACT

A method of treating pruritus (itching) in a subject in need thereof is carried out by administering the subject an active agent in a treatment effective amount, wherein the active agent is a superoxide dismuate (SOD) mimetic. The SOD mimetic can be a complex of a metal (e.g., manganese) and an organic ligand, with suitable organic ligands including porphyrins, polyamines, salens, nitroxides, and fullerenes. Compositions for carrying out such methods are also described.

15 Claims, 3 Drawing Sheets

(56) References Cited

U.S. PATENT DOCUMENTS

| | | |
|---|---|---|
| 2011/0184016 A1 | 7/2011 | Lerner et al. |
| 2011/0262511 A1 | 10/2011 | Love et al. |
| 2012/0065181 A1 | 3/2012 | Warner et al. |
| 2013/0195985 A1 | 8/2013 | Lepelletier et al. |
| 2016/0113940 A1 | 4/2016 | Crapo et al. |
| 2016/0324867 A1 | 11/2016 | Crapo et al. |

OTHER PUBLICATIONS

Li et al. Enzyme Research (2011) vol. 2011, pp. 1-6.*
Garibyan et al. Dermatol. (2013) vol. 26, pp. 1-13.*
Miriyala et al. Biochimica et Biophysica Acta (2012) vol. 1822, pp. 794-814.*
International Search Report and Written Opinion, PCT/US2015/012228, dated Apr. 10, 2015.
International Search Report and Written Opinion, PCT/US2015/012231, dated Apr. 7, 2015.
Batinic-Haberle et al. "Superoxide Dismutase Mimics: Chemistry, Pharmacology, and Therapeutic Potential" *Antioxidants & Redox Signaling* 13(6):877-917 (2010).
Huynh, Tu T. "Burden of Disease: The Psychosocial Impact of Rosacea on a Patient's Quality of Life" *American Health & Drug Benefits* 6(6):348-354 (2013).
Liu et al. "Oxidative stress induces itch via activation of transient receptor potential subtype ankyrin 1 (TRPA1) in mice" *Neuroscience Bulletin* 28(2):145-154 (2012).
Makinde et al. "Effect of a Metalloporphyrin Antioxidant (MnTE-2-PyP) on the Response of a Mouse Prostate Cancer Model to Radiation" *Anticancer Research* 29:107-118 (2009).
Mathur et al. "Physical and chemical penetration enhancers in transdermal drug delivery system" *Asian Journal of Pharmaceutics* 4(3):173-183 (2010).
Musk et al. "Chemical Countermeasures for the Control of Bacterial Biofilms: Effective Compounds and Promising Targets" *Current Medicinal Chemistry* 13:2163-2177 (2006).
Oberley-Deegan et al. "The Antioxidant Mimetic, MnTE-2-PyP, Reduces Intracellular Growth of *Mycobacterium abscessus*" *American Journal of Respiratory Cell and Molecular Biology* 41:170-178 (2009).
Panthan et al. "Chemical Penetration Enhancers for Transdermal Drug Delivery Systems" *Tropical Journal of Pharmaceutical Research* 8(2):173-179 (2009).
Rogers et al. "Tandem dispersion and killing of bacteria from a biofilm" *Organic & Biomolecular Chemistry* 7:603-606 (2009).
Roosta et al. "Skin Disease and Stigma in Emerging Adulthood: Impact on Healthy Development" *Journal of Cutaneous Medicine and Surgery* 14(6):285-290 (2010).
Tyle, Praveen "Iontophoretic Devices for Drug Delivery" *Pharmaceutical Research* 3(6):318-326 (1986).

\* cited by examiner

METHODS OF TREATING PRURITUS

RELATED APPLICATIONS

This application is a 35 U.S.C. § 371 national phase entry of PCT Application PCT/US2015/012228, filed Jan. 21, 2015, and published in English on Jul. 30, 2015, as International Publication No. WO 2015/112586, and which claims the benefit of U.S. Provisional Patent Application Ser. No. 61/930,132, filed Jan. 22, 2014, the disclosure of each of which is incorporated by reference herein in its entirety.

FIELD OF THE INVENTION

The present invention concerns methods and composition useful for the treatment of Pruritus (itch).

BACKGROUND OF THE INVENTION

"Itch" is an unpleasant condition on the skin surface, generally defined as a sensation that causes or leads a subject or patient to scratch the area or location on the subject where the sensation is perceived. Chronic itch is a common problem associated with skin disease, systemic disease, metabolic disorders, and other conditions. See generally T. Liu and R.-R. Ji, *Neurosci. Bull.* 28: 145-154 (2012), Numerous different treatments have been suggested. See, e.g., J. Speight, PCT Patent App. WO 97/35573 (Oct. 2, 1997); T. Jung and J. Meingassner, PCT Patent App. WO 2008/129000; and E. Lerner and V. Reddy, US Patent App. US 2011/0184016 (Jul. 28, 2011). Because the consequences of scratching can exacerbate the sensation of itch, and lead to other problems such as infection, there remains a need for new methods and compositions for the treatment of pruritus.

SUMMARY OF THE INVENTION

A first aspect of the present invention is a method of treating pruritus (itching) in a subject in need thereof, comprising administering the subject a porphyrin active compound or active agent as described herein in a treatment effective amount.

A further aspect of the invention is an active compound as described herein for use in carrying out a method as described herein, or for the preparation of a medicament for carrying out a method as described herein.

The foregoing and other objects and aspects of the present invention are explained in greater detail in the specification set forth below.

DETAILED DESCRIPTION OF PREFERRED EMBODIMENTS

Figure 2:
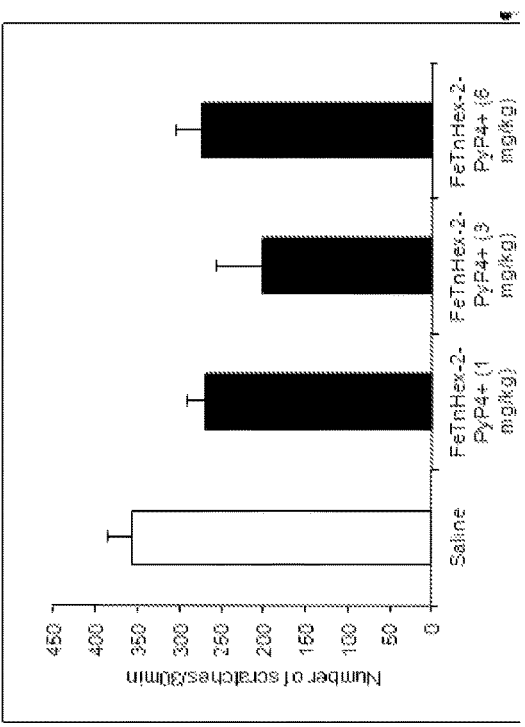
FIG. 2 shows frequency of scratching in compound 48/48-treated mice administered the iron porphyrin FeTnHex-2-Pyp4+.

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

"Treat" as used herein refers to any type of treatment that imparts a benefit to a patient or subject matter as described herein, particularly delaying or retarding the onset or progression of the conditions described herein, or reducing the severity of symptoms, or speeding or improving recovery therefrom. The treatment may be sufficient to reduce the frequency of scratching a region afflicted by itch by the subject, or the urge or desire of the subject to scratch a region afflicted with an itch.

"Pharmaceutically acceptable" as used herein means that the compound or composition is suitable for administration to a subject to achieve the treatments described herein, without unduly deleterious side effects in light of the severity of the disease and necessity of the treatment.

"Combination" as used herein with respect to a method of administration (e.g., an active compound and an antibiotic administered in combination) includes administering the the two or more compounds simultaneously, or sequentially, sufficiently close in time to produce a combined therapeutic or treatment effect.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, Cert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, acyloxy, arylalkyloxy, heterocyclooxy, heterocyclolalkyloxy, mercapto, alkyl-S(O)$_m$, haloalkyl-S(o)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkyl amino, cycloalkylamino, cyclo alkyl alkylamino, acylamino, arylalkylamino, hetero cycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon group containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2- butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooetyl. These rings may be optionally substituted with additional substituents as described herein such as halo or loweralkyl. The term "cycloalkyl" is generic and intended to include heterocyclic groups as discussed below unless specified otherwise, "Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, aryl amino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl, "Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a eompounnd of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

1. Active Agents

Active compounds or active agents of the present invention are, in general, superoxide dismutase (SOD) mimetics (also referred to as "SOD mimics"). Such compounds are known and described in, for example, .I. Batinic-Haberle et al., Superoxide Dismuates Mimics: Chemistry, Pharmacology, and Therapeutic Potential, *Antioxidants & Redox Signaling*, 13, 877-918 (2010). Additional examples include, but are not limited to, those set forth in U.S. Pat. No. 8,486,928 to Riley, U.S. Pat. No. 8,217,166 to Salvemini et al., U.S. Pat. No. 8,003,636 to Klimko et al., and U.S. Pat. No. 5,223,537 to Fridovich et al., and in PCT Application Publication No. WO 2013071059 to Kash et al. In some embodiments, such SOD mimetics are metal complexes, such as manganese complexes (e.g., Mn(III) and Mn(II) complexes) with an organic ligand. Examples include, but are not limited to, metal (such as manganese) complexes with porphyrins, polyamines, salens (including salen derivatives), nitroxides, and fullerenes. In preferred embodiments, the active SOD mimetic compounds are-prophryin compounds, and/or redox active porphyrin compounds.

Examples of porphyrin active compounds, and methods of making the same, include but are not limited to those set forth in U.S. Pat. No. 8,470,808 to Piganelli et al.; U.S. Pat. No. 8,183,364 to Batinic-Haberle et al., U.S. Pat. No. 6,916,799 to Fridovich et al.; U.S. Pat. No. 6,479,477 to Crapo et al.; U.S. Pat. No. 6,583,132 to Crapo et al. and in US Patent Application Pub. No. US 2012/0065181 to Warner et al.; the disclosures of which are incorporated by reference herein in their entirety.

Examples of active compounds include but are not limited to compounds of Formula I:

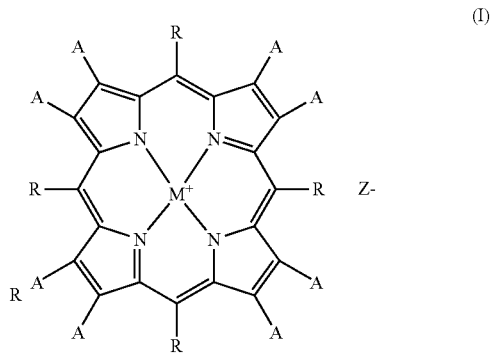

wherein:

each R is independently substituted or unsubstituted aryl, heteroaryl, cycloalkyl, or heterocycloalkyl;

each A is an independently selected hydrogen, or an electron-withdrawing or electron donating group (e.g., e.g., is halogen, NO$_2$ or CHO), M is a metal, e.g., selected from the group consisting of manganese, iron, copper, cobalt, nickel and zinc, or is absent (in which case a hydrogen is added to each of the two nitrogens required to correct valency), and Z$^-$ is a counterion.

In some embodiments of Formula I above, each R is preferably heteroaryl or heterocycloalkyl, particularly those containing at least one or two nitrogen atoms in the heterocyclic ring (e.g., pyrrolyl, imidazolyl, triazolyl, pyridyl, pyrimidyl, triazinyl, oxazolyl, thiazolyl, oxazinyl, thiazinyl, oxathiazinyl, etc.), in some embodiments wherein at least one of which nitrogen atoms (or in some embodiments at least two of which nitrogen atoms) are optionally but preferably substituted (e.g., quaternized) with a substituent such as described in connection with heterocyclic groups above (e.g., substituted with alkyl, alkoxyalkyl, etc.).

Still more particular examples of the foregoing active compounds include but are not limited to those set forth below.

A. Alkyl Substituted Imidazole Porphyrins. In some embodiments the active compound has a structure of Formula A1 or A2:

(A1)

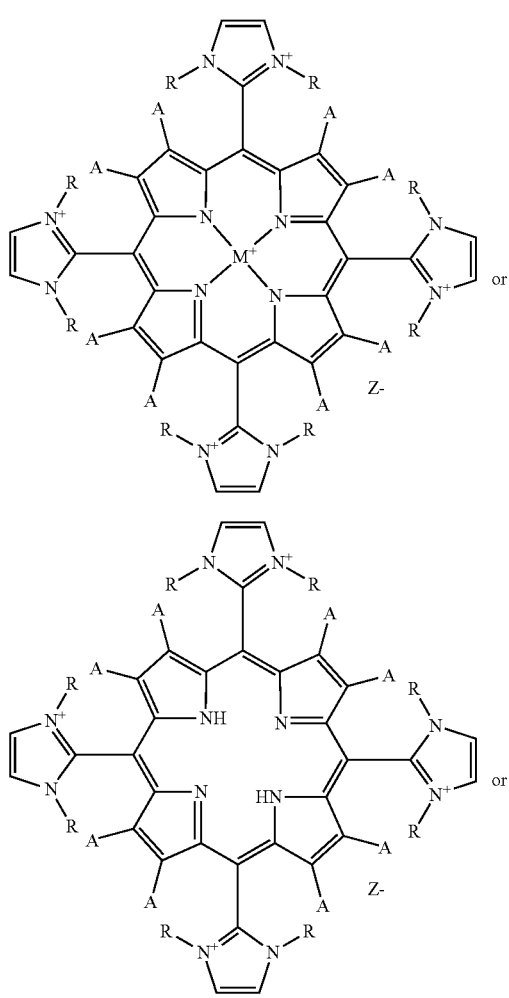

(A2)

wherein:
each R is $C_{1-12}$ alkyl (straight chain or branched), more preferably $C_{2-6}$ alkyl, and most preferably ethyl, propyl, butyl, or pentyl (straight chain or branched);
each A is, independently, hydrogen or an electron withdrawing group (e.g., halogen, $NO_2$ or CHO),
M is metal selected from the group consisting of manganese, iron, copper, cobalt, nickel and zinc, and
$Z^-$ is a counterion.
In some embodiments the active compound has the formula:

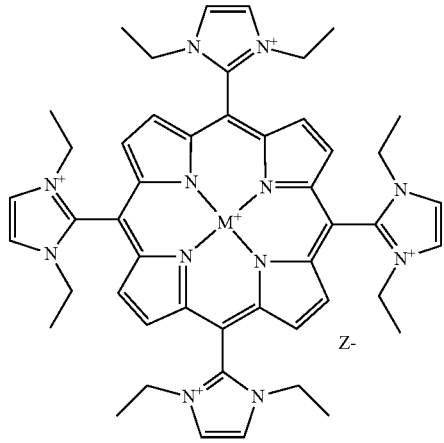

wherein Z– is a counterion.

B. Alkyl Substituted Pyridyl Porphyrins In some embodiments the active compound has a structure of Formula B1 or B2:

(B1)

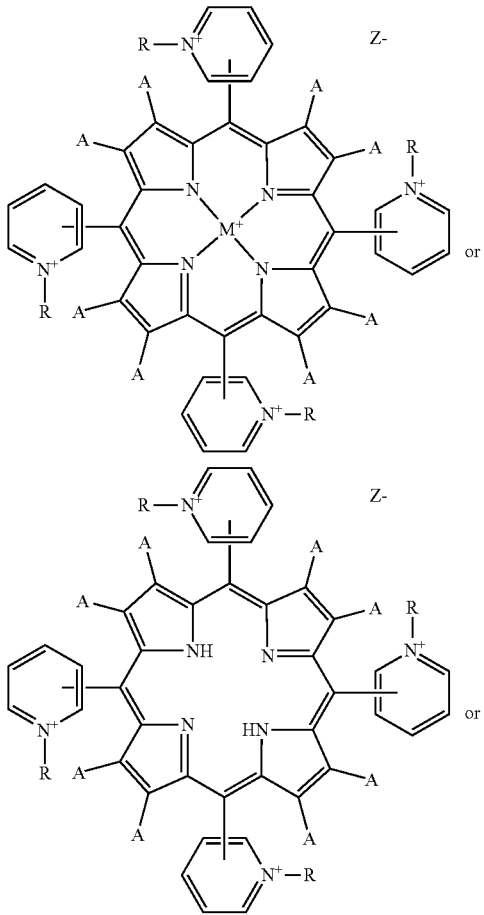

(B2)

wherein:
each R is $C_{1-12}$ alkyl (straight chain or branched), more preferably $C_{2-6}$ alkyl, and most preferably ethyl, propyl, butyl, or pentyl (straight chain or branched);
each A is, independently, hydrogen or an electron withdrawing group (e.g., halogen, $NO_2$ or CHO),
M is metal selected from the group consisting of manganese, iron, copper, cobalt, nickel and zinc, and
$Z^-$ is a counterion.
In some embodiments the compound has a structure of the Formula V:

V

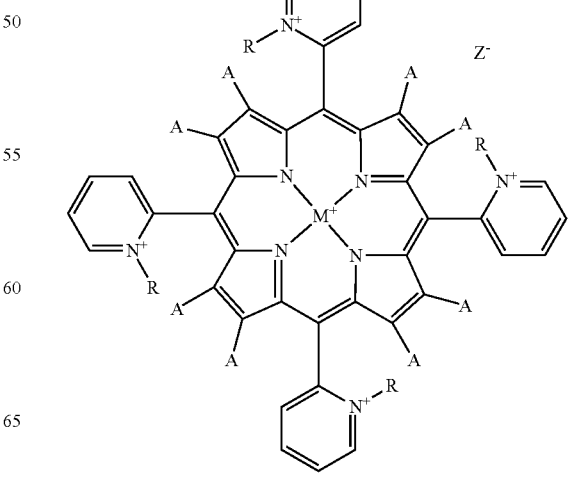

wherein each R, A, M and Z is as given in connection with Formula B1 and B2 above.

In some embodiments the compound has the structure:

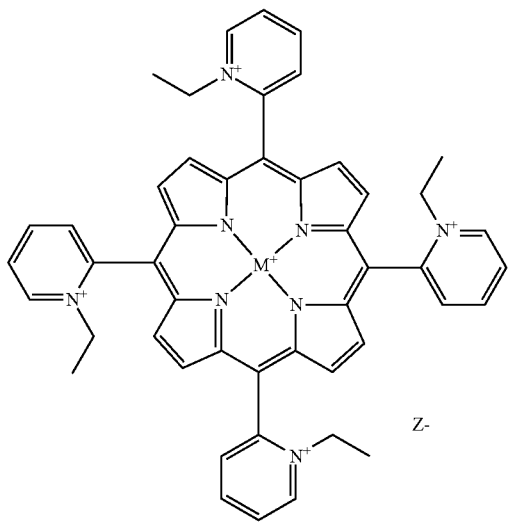

wherein $Z^-$ is a counterion.

C. Alicoxyalkyl Substituted Pyridyl Porphyrins. In some embodiments the active compound has a structure of Formula C1 or C2:

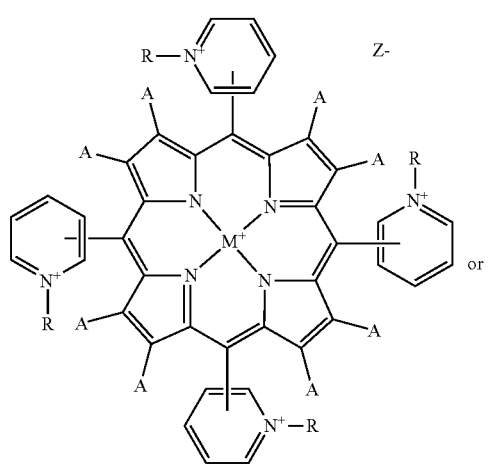
(C1)

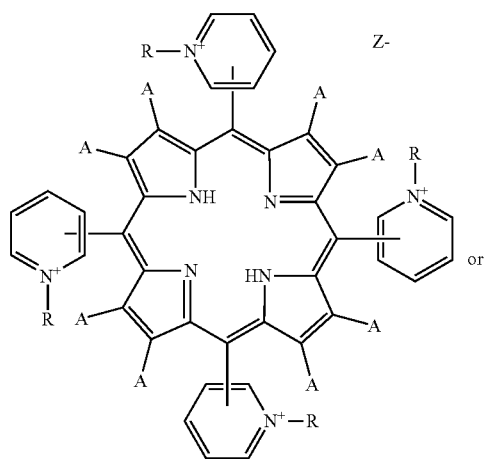
(C2)

wherein:
each R is —$(CH_2)_mCH_2OX$;
m is 1 or 2, preferably 1;

X is $C_{1-12}$ alkyl (straight chain or branched), more preferably $C_{2-6}$ alkyl, and most preferably ethyl, propyl, butyl, or pentyl (straight chain or branched).

each A is, independently, hydrogen or an electron withdrawing group (e.g., halogen, $NO_2$ or CHO), M is metal selected from the group consisting of manganese, iron, copper, cobalt, nickel and zinc, and $Z^-$ is a counterion.

In some embodiments the compound has a structure of the Formula V:

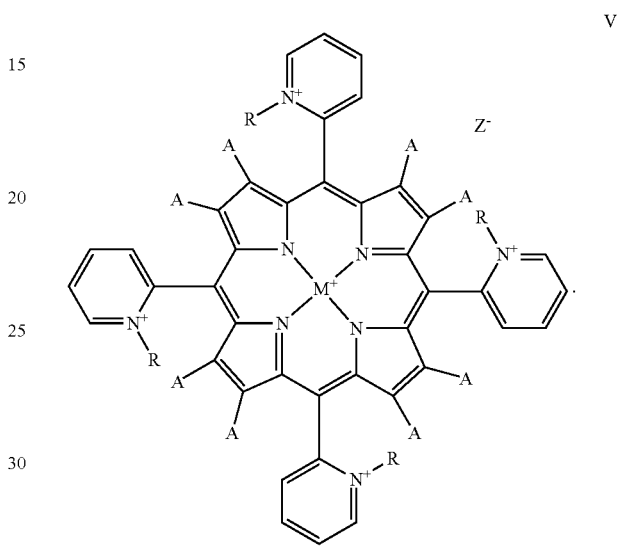
V wherein each R, A, M and Z is as given in connection with Formula C1 and C2 above.

In some embodiments the compound has the structure:

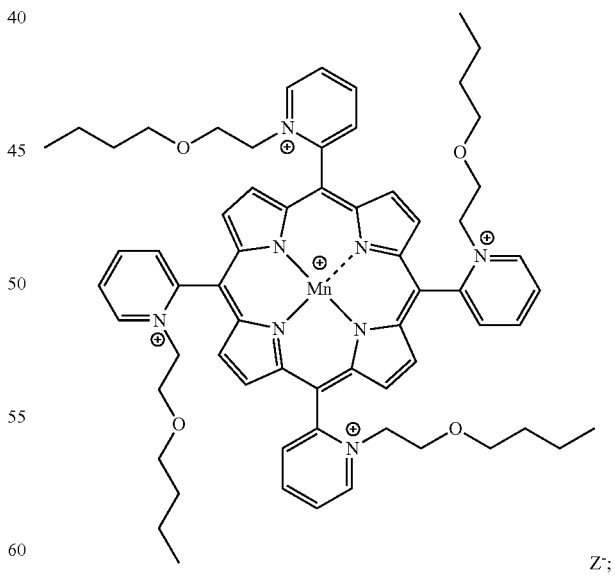

wherein $Z^-$ is a counterion.

D. Salts. The active compounds disclosed herein can, as noted above, be prepared in the form of their salts or pharmaceutically acceptable salts, e.g. to provide a compound or composition including a counterion as noted above. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations

The active compounds described above may be formulated for administration in a pharmaceutical carrier in accordance with known techniques, See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alfa, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques. Of course, the liposomal formulations containing the compounds disclosed herein or salts thereof may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidylcholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multi-dose use. Of course, as indicated, the pharmaceutical compositions of the present invention may be lyophilized using techniques well known in the art.

Topical Formulations. As noted above, the active compound(s) of this application can be prepared as topical formulations. For a general review of topical formulations see, for example, Topical Drug Delivery Systems: A Review: pharmainfo.net, volume 6(5) 2008, incorporated herein in its entirety. The active compound(s) of this application can be topically formulated for external or internal use. External topicals are spread, sprayed or otherwise dispersed onto cutaneous tissue to cover the affected area. Internal topicals are typically prepared for application to the mouth, vaginal or anorectal tissue.

Topical formulations (or drug delivery systems) are typically classified by their physical state and include: solids, including but not limited to, powders, aerosols, sprays and plasters; liquids, including but not limited to, lotions, liniments, solutions, emulsions, oils, suspensions and aerosols; and semi-solids, including but not limited to, ointments, creams, pastes, gels, jellies and suppositories.

In some embodiments, the carriers and vehicles include, but are not limited to, micro or nanocapsules, nanoemulsions/submicron emulsions/miniemulsions, solid lipid nanoparticles, multiple emulsions, microemulsions. Vesicular carriers include, but are not limited to, liposomes, niosomes, transfersomes, ethosomes, and aquasomes. Chemical penetration enhancers include, but are not limited to, sulfoxides and similar chemicals, azone, pyrrolidones, fatty acids, essential oils terpenes and terpenoids, oxazolidinones, ureas, water, alcohols, fatty alcohols, and glycerols, and surfactants, see, for example, Mathur, V. et al., Physical and chemical penetration enhancers in transdermal drug delivery system, Asian J. Pharm., 4:173-83 (2010) and Escobar-Chavez, J. J. et al in Pharmacology edited by Luca Gallelli (2012) incorporated herein by reference in their entireties.

In some embodiments the topical formulation comprises chemical penetration enhancers. Chemical penetration enhancers include, but are not limited to solvents, surfactants, and chemicals. Examples of solvents include, but are not limited to, water, alcohols such as methanol and ethanol, alkyl methyl sulfoxide, dimethyl sulfoxide, alkyl homologs of methyl sulfoxide such as dimethyl acetamide, and dimethylformamide; pyrrolidones such as 2-pyrrolidone, N-methyl, and 2-pyrrolidone; laurocapran (Azone), propylene glycol, glycerol, silicone fluids and isopropyl palmitate. Examples of surfactants include anionic surfactants including, but not limited to, dioctyl sulphosuccinate, sodium lauryl sulfate and decodecylmethyl sulphoxide; cationic surfactants; and nonionic surfactants such as Pluronic F127 and Pluronic F68. Other chemical penetration enhancers include bile salts such as sodium taurocholate, sodium deoxycholate and sodium tauroglycocholate; binary systems such as propylene glycol/oleic acid and 1,4-butanediol/ linoleic acid; and chemicals such as N,N-diethyl-m-toluamide and calcium thioglycolate.

In another embodiment the topical formulation comprises chemical penetration enhancers including, but not limited to N-methyl-2-pyrolidone, glycols such as diethylene glycol, propylene glycol and tetraethylene glycol, fatty acids including, but not limited to, laurie, myristic and capric, nonionic surfactants including, but not limited to, polyoxyethylene-2-oleyl ether and polyoxyethylene-2-stearyl ether. In another embodiment essential oils of eucalyptus, chenopodium and ylang-ylang are used. In one embodiment L-menthol, terpenes, oxazolidinones, and ureas are used as chemical penetration enhancers see, for example, Pathan, I. B. et al., Tropical J. Pharm. Res., 8(2):173-179 (2009).

In other embodiments the topical formulations comprise common topical ingredients that include, but are not limited to, vehicles such as hydrophobic vehicles, water-miscible vehicle co-solvents, structural matrix formers; suspending, jelling, or viscosity inducing agents, water-in-oil emulsifiers, preservatives, and chelating agents.

In some embodiments, hydrophobic vehicles include hydrocarbons such as liquid petrolatum (mineral oil, liquid paraffin, paraffin oil), white petrolatum (petroleum jelly, Vaseline), yellow petrolatum (petroleum jelly), and squalane (perhydrosqualene, spinacane); silicones such as liquid polydimethylsiloxanes (dimethicone, silastic, medical grade silicone oil); alcohols such as lauryl alcohols (1-dodecanol, dodecyl alcohols), myristyl alcohols (tetradecanol, tetradecyl alcohols) cetyl alcohols (hexadecanol, ethal, palmityl alcohols), stearyl alcohols (stenol, cetosteryl alcohols) and oleyl alcohols (ocenol); sterols and sterol esters, including, but not limited to, lanolin (hydrous wool fat, lanum), anhydrous lanolin (wool fat, anhydrous lanum, agnin), and semi synthetic lanolin's; carboxylic acids such as lauric acid, myristic acid, palmitic acid, stearic acid and oleic acid; esters and polyesters including, but not limited to, cholesterol esters (stearate), ethylene glycol monoesters, propylene glycol monoesters, glyceryl monoesters, glyceryl monostearate, sorbitol monoesters, sorbitain monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, and isopropyl palmitate; ethers and polyethers such as polyethylene-polypropylene glycols (pluronics).

In another embodiment, water-miscible vehicle co-solvents include polyols and polyglycols such as propylene glycol (1,2-propanediol), glycerin (glycerol), liquid polyethylene glycol, solid polyethylene glycol (hard macrogol, carbowax) and 1,2-phenols-hexanetriol, sorbitol solution 70%; esters and polyesters such as polyoxyethylene sorbitain monoesters (stearate-tweens) and polyoxy ethylene sorbitan polyesters (tweens); ethers and polyethers, including but not limited to, polyethylene glycol monocetyl ether (cetomacrogol 1000) and polyethylene-polypropylene glycols (pluronics).

In other embodiments, structural matrix formers include but are not limited to hydrocarbons, silicones, polyols and polyglycols, alcohols, sterols and sterol esters, carboxylic acids, esters and polyesters. Examples of hydrocarbons include, but are not limited to, white petrolatum (petroleum jelly, Vaseline), yellow petrolatum (petroleum jelly), paraffin (paraffin wax, hard paraffin), microcrystalline wax and ceresin (mineral wax, purified ozokerite). Examples of silicones include, but are not limited to fumed silica (cab-O-sil), bentonite (colloidal aluminum silicate) and veegum (colloidal magnesium aluminum silicate). Examples of polyols and polyglycols include, but are not limited to solid polyethylene glycol (hard macrogol, carbowax). Examples of alcohols include, but are not limited to, cetyl alcohols (hexadecanol, ethyl, palmityl alcohols) and stearyl alcohols (stenol, cetosteryl alcohols). Examples of sterols and sterol esters include, but are not limited to, cholesterol (cholesterin), lanolin (hydrous wool fat, lanum), anhydrous lanolin (wool fat, anhydrous lanum, and agnin), and semi-synthetic lanolin's. Examples of carboxylic acids include, but are not limited to, lauric acid, myristic acid, palmitic acid, stearic acid, and oleic acid. Examples of esters and polyesters include, but are not limited to, bees wax, white bees wax (bleached bees wax), carnauba wax, myricin, cholesterol esters (stearate), polyoxyethylene sorbitain, monoesters (stearate- tweens), lard, and hydrogenated oils.

In another embodiment suspending, jelling or viscosity inducing agents include silicones, polycarboxylates, polysulfates, polysaccharides and other compounds. Silicones include, but are not limited to, fumed silica (cab-O-sil), bentonite (colloidal aluminum silicate) and veegum (colloidal magnesium aluminum silicate). Polycarboxylates, polysulfates and polysaccharides include, but are not limited to, agar, alginates, carrageen, acacia, tragacanth, methylcellulose, carboxy methylcellulose, hydroxy ethyl cellulose, carboxy vinyl polymer, gelatin, pectin, xanthan, and polyacrylic acid. Other compounds include, but are not limited to, ethanolamine and triethanolamine.

In some embodiments, water-in-oil (w/o) emulsifiers include but are not limited to, sterols and sterol esters, carboxylic acids, ether and polyethers. Sterols and sterol esters include, but are not limited to, cholesterol (cholesterin),lanolin (hydrous wool fat, lanum), anhydrous lanolin (wool fat, anhydrous lanum, agnin), and semi-synthetic lanolin's. Carboxylic acids include, but are not limited to, the $Na^+$, $K^+$ and ethanolamine salts of lauric acid, myristic acid, palmitic acid, stearic acid, and oleic acid. Ethers and polyethers include, but are not limited to, polyethylene-polypropylene glycols (pluronics).

In another embodiment, oil-in-water (o/w) emulsifiers include, but are not limited to, esters and polyesters, ethers and polyethers and other miscellaneous reagents. Esters and polyesters, include, but are not limited to, polyoxyethylene sorbitain monoesters (stearate-tweens), polyoxy ethylene esters (stearate-polyethylene glycol monoesters, Myrj), and polyoxy ethylene sorbitan polyesters (tweens). Ethers and polyethers, but are not limited to, polyethylene glycol monocetyl ether (cetomacrogol 1000) and polyethylene-polypropylene glycols (pluronics). Other miscellaneous reagents, but are not limited to, sodium lauryl sulfate, Borax (sodium borate), ethanolamine and triethanolamine.

In still another embodiment, preservatives include antimicrobials such as benzalkonium chloride, benzoic acid, benzyl alcohol, bronopol, chlorhexidine, chlorocresol, imidazolidinyl urea, paraben esters, phenol, phenoxyethanol, potassium sorbate, and sorbic acid. Preservatives also include antioxidants such as α-tocopherol, ascorbic acid, ascorbyl palmitate, butylated hydroxyanisole, sodium ascorbate, and sodium metabisulfite.

In one embodiment, chelating agents include but are not limited to, citric acid and edetic acid. The chelating agents can be combined with buffers produced from reagents such as phosphoric acid, $NaH_2PO_4$, glycine, acetic acid, triethanolamine and boric acid. In another embodiment, chelating agents can be combined with humectants including, but not limited to, glycerin, propylene glycol, glyceryl triacetate, sorbitol, xylitol, maltitol, polydextrose, quillaia, lactic acid, urea, and lithium chloride.

In one embodiment, ointments comprise active compound(s) in ointment bases. Ointment bases are typically classified by the USP into four general groups (a) hydrocarbon bases including but not limited to, petrolatum, USP; white petrolatum, USP; yellow petrolatum, USP; white petrolatum, USP; (b) absorption bases that include water-in-oil emulsions (c) water-removable bases that include hydrophilic ointment, USP; and (d) water-soluble bases such as polyethylene glycol ointment, NF.

In another embodiment, creams comprise active compound(s) dissolved or suspended in water removable or emollient bases. Creams are classified as water-in-oil or oil-in-water. There are several types of creams including but not limited to cleaning and cold cream or lotion, vanishing and foundation cream, night and massage cream, hand and body cream, all purpose cream, and moisturizing cream. Examples of cream bases include (a) cream base, w/o (rose water ointment) oleaginous phase including but not limited to, spermaceti, white wax, almond oil, sodium borate and an aqueous phase including but not limited to, sodium borate, stronger rose water, NF, and water (b) cream base o/w including an oleaginous phase including but not limited to, stearyl alcohol, beeswax and sorbitan monooleate, and an aqueous phase including but not limited to, sorbitol solution, polysorbate 80, methyl paraben, and water (c) cream base, o/w (vanishing cream) including an oleaginous phase including, but not limited to, stearic acid, stearyl alcohol, cetyl alcohol and an aqueous phase including but not limited to, glycerin, methyl paraben, propyl paraben, potassium hydroxide, and water.

In another embodiment, active compound(s) can be formulated as a paste or gel. Examples of gelling agents include, but are not limited to, synthetic macromolecules such as Carbomer 934 and cellulose derivatives such as carboxymethylcellulose and hydroxypropyl methylcellulose. In one embodiment, gels include single phase and double phase gels.

In one embodiment, active compound(s) can be formulated as a jelly. In one embodiment, jellies are water-soluble bases typically prepared from natural gums such as tragacanth, pectin, alginate and boroglycerin or from synthetic derivatives of natural substances such as methylcellulose and carboxymethylcellulose.

In some embodiments, the active compound(s) can be formulated as a lotion or liniment. Examples of lotions include, but are not limited to, hand lotions, face lotions and body lotions. Lotions can comprise alcohols such as ethyl alcohol, antiseptics, emollients and haemostypic substances. In another embodiment, lotions comprise extract of witch-hazel, menthol, glycerin, boric acid, alum, potassium oxyquinoline; sulfate and chloro form.

In one embodiment, active compound(s) can be formulated as a suppository. In same embodiments, suppositories comprise bases including, but not limited to, cocoa butter, glycerin, hydrogenated vegetable oils, and polyethylene glycol.

In some embodiments, the active compound(s) can be formulated as a powder. In another embodiment, powders include, but are not limited to, body powder, dusting powder, talcum powder, face powder, and medicated powders.

In some embodiments, the active compound(s) can be formulated as a solution. In an embodiment, solvents used to prepare solutions include, but are not limited to, water, ethyl alcohol and propylene glycol.

In another embodiment, the active compound(s) can be formulated as an emulsion. In some embodiments, emulsions include, but are not limited to, water-in-oil, oil-in-water, water-in-oil-in-water and oil-in-water-in-oil.

In one embodiment, the active compound(s) can be formulated as a suspension. In some embodiments, suspensions include, but are not limited to, flocculated and deflocculated suspensions.

In some embodiments, the active compound(s) can be formulated in the form of an aerosol. In one embodiment, topical aerosols comprise hydrocarbons (propane, butane and isobutene), and compressed gases such as nitrogen, carbon dioxide and nitrous oxide.

In some embodiments, a healing ointment such as Aquaphor® can be employed in conjunction with the topical formulation. See, U.S. Pat. No. 7,976,854 to Hattendorf et al. incorporated herein in its entirety.

In some embodiments the active compound(s) can be formulated with VersaBase Cream, VersaBase Foam, VersaBase Gel, VersaBase Lotion, or VersaBase Shampoo.

In some embodiments the active compound(s) can be formulated as a spot-on formulation. See, U.S. Pat. No. 7,531,186 to Boeckh et al. incorporated herein in its entirety. In one embodiment, the topical formulation comprises the active compound(s), a liquid carrier vehicle and optionally a crystallization inhibitor. In some embodiments, the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethylene glycol monoethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of ethanol, isopropanol or methanol; and optionally a crystallization inhibitor selected from the group consisting of an anionic surfactant, a cationic surfactant, a non-ionic surfactant, an amine salt, an ampho- teric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

In certain embodiments a topical formulation comprises: an active compound, a pharmaceutically acceptable dipolar aprotic solvent or an acid; and a pharmaceutically acceptable aqueous secondary solvent. See, U.S. Pat. No. 6,844,004 to Anderson herein incorporated by reference. In some embodiments, the acid is a carboxylic acid and is exemplified by acetic acid. In other embodiments, the acid is hydrochloric acid. In some embodiments, the aqueous secondary solvent is a surfactant. Surfactants are well known in the art and are organic lipid compounds that are normally produced by the lung tissue and help with the opening of the alveolar constrictions during breathing. Surfactants are also commercially available. In still other embodiments the aqueous secondary solvent is an aqueous lipid emulsion. The aqueous lipid emulsion can comprise a lipid component that includes at least one vegetable oil and at least one fatty acid. Such a lipid component can comprise at least about 5% by weight soybean oil and at least about 50% by weight fatty acids. In some embodiments, the lipids in the composition are preferably present in a form other than liposomes, for example, at least about 50% by weight of the lipid is not in the form of liposomes, more preferably a least about 75%, and most preferably at least about 95%. In other embodiments the secondary solvent can be water, a saline solution, or a dextrose solution. In some embodiments, the composition further comprises an ointment and/or a cream base. The ointment base can comprise one or more of petrolatum, mineral oil, ceresin, lanolin alcohol, panthenol, glycerin, bisabolol, cocoa butter and the like, The ointment or cream can be any commonly known commercially available ointments or creams such as Aquaphor™ or Eucerin™.

4. Conditions for Treatment

The methods and compositions described herein may be used to treat any type of itch, including but not limited to dermal or pruritoceptive itch, neuropathic itch, neurogenic itch, and psychogenic itch.

Thus the sensation of itch to be treated by the methods and compositions described herein may arise from any cause, including but not limited to scabies, swimmer's itch, athlete's foot (or other fungal infections), allergic reaction to contact with specific chemicals, such as urushiol (e.g., from poison ivy or poison oak), infestations such as with head and body lice, cutaneous larva migrans, herpes and chickenpox, insect bites (such as from mosquitos and chiggers), photodermatitis, hives or urticaria, dandruff, punctate palmoplantar keratoderma, scab healing, scar growth, skin conditions such as psoriasis, eczema, sunburn, and hidradenitis suppurativa; xerosis (dry skin), diabetes mellitus, hyperparathyroidism, iron deficiency anemia, jaundice and cholestasis, cancers or malignancies such as lymphoma or Hodgkin's disease, menopause, polycythemia, throid illness, uraemia or uremic Pruritus; drugs that activate histamine receptors or trigger histamine release such as opioids and chloroquine, Gestational pemphigoid, Intrahepatic cholestasis of pregnancy, Pruritic urticarial papules and plaques of pregnancy, pscyriatric disease or hallucinations, etc.

In addition to human disorders, the invention may be used to treat itch in animals for veterinary purposes as noted above. Examples of particular conditions include sweet itch, summer itch, Queensland itch, summer eczema, or summer seasonal recurrent dermatitis in horses, ponies, and donkies; environmental, nutritional, parasitic, allergic, neurogenic and infectious itch in dogs and cats; mange in general in dogs, cats, cattle, etc.

4. Dosage and Routes of Administration

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The effective amount (e.g., therapeutically effective or treatment effective amount) or dosage of any specific active compound as described herein, for use in any specific method as described herein, will vary depending on factors such as the condition being treated, the route of administration, the general condition of the subject (e.g., age, gender, weight, etc.), etc. In general (e.g., for oral or parenteral administration), the dosage may be from about 0.01, 0.05, or 0.1 milligram per kilogram subject body weight (mg/kg), up to about 1, 5, or 10 mg/kg. For topical administration, the active agent may be included in a pharmaceutically acceptable composition to be applied in any suitable amount, typically from 0.01, 0.1, or 1 percent by weight, up to 10, 20, or 40 percent by weight, or more, of the weight of the composition, again depending on factors such as the condition being treated, condition of the subject, etc.

The active agents described herein may be administered directly or through the administration to the subject of a pharmaceutically acceptable prodrug which is in turn converted to the active agent in vivo. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The present invention is explained in greater detail in the following non-limiting Examples.

EXAMPLE 1

Parenteral Injection in Animal Itch Model

Figure 1:
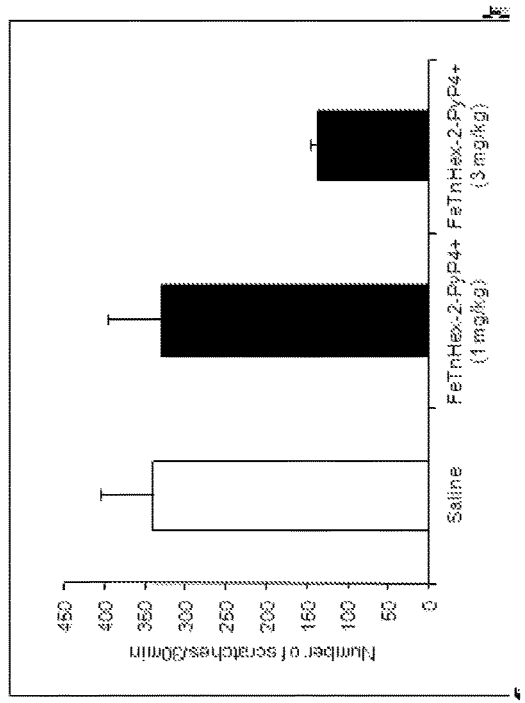
FIG. 1 shows frequency of scratching in chlorquinone-treated mice administered the iron porphyrin FeTnHex-2-Pyp4+.
Figures 3, 4:
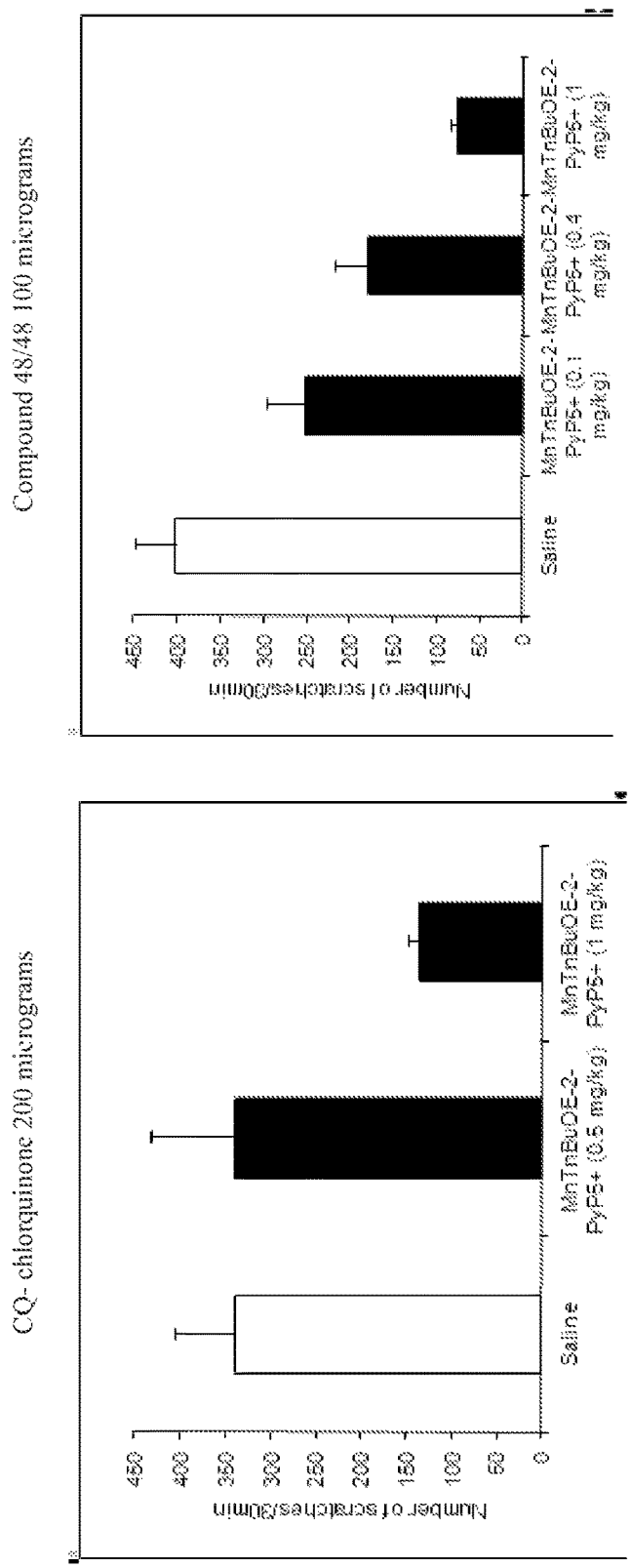
FIG. 3 shows frequency of scratching in chlorquinone-treated mice administered the manganese porphyrin MnTnBuOE-2-PyP$^{5+}$.
FIG. 4 shows frequency of scratching in compound 48/48-treated mice administered the manganese porphyrin MnTnBuOE-2-PyP$^{5+}$.
Figure 6:
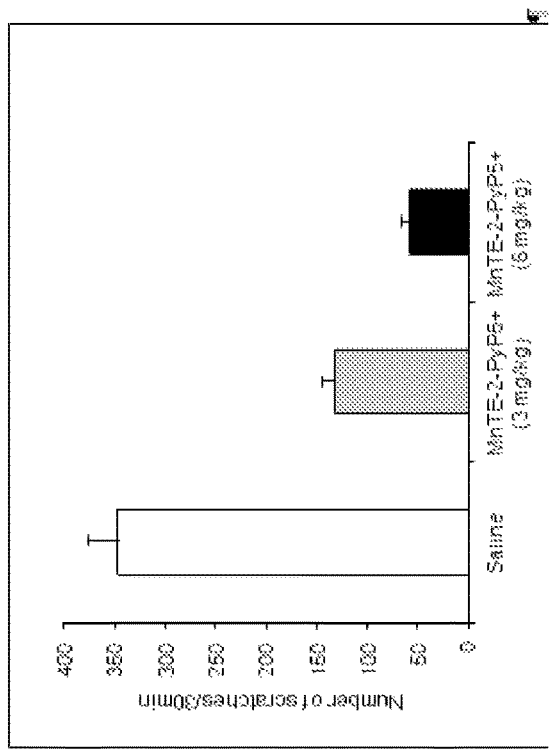
FIG. 6 shows frequency of scratching in compound 48/48-treated mice administered the the manganese porphyrin MnTnHex-2-PyP5+.
Figure 5:
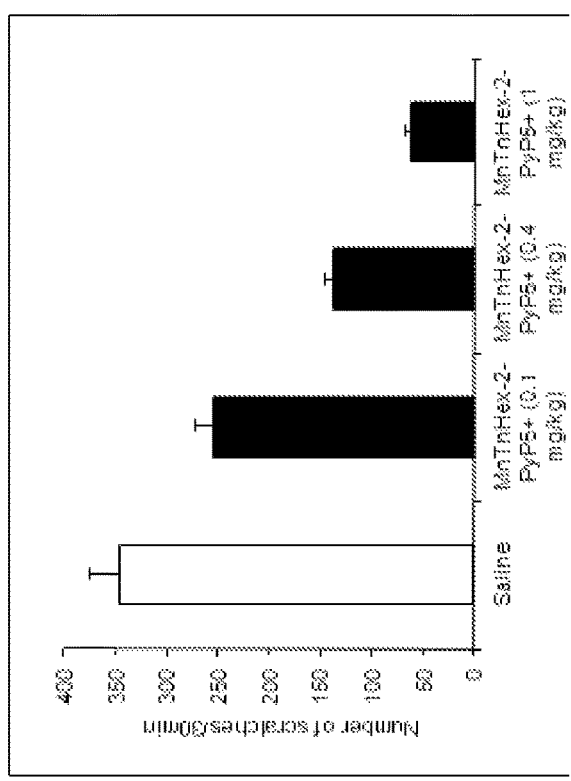
FIG. 5 shows frequency of scratching in chlorquinone-treated mice administered the the manganese porphyrin MnInHex-2-PyP5+.

Active compounds as described herein were administered to animals by intraperitoneal injection in the in vivo itch model described in Tong Liu and Ru-Rung Ji, *Neurosei Bull.* 28(2): 145-154 (2012), as follows: CQ-chlorquinonc 200 micrograms; Compound 48/48 100 micrograms; Ip injections of manganese porphyrins (MnP) and iron porphyrins (FeP), Data is given in the graphs provided as FIGS. 1 to 6 herein. In the figures, "MnTnBuOE-2-PyP$^{5+}$" refers to Manganese ortho tetrakis(N-n-butoxyethylpyridinium-2-yl)porphyrin, "MnTnHex-2-PyP5+" refers to ortho Mn(III) meso-tetrakis(N-n-Hexylpyridinium-2-yl)porphyrin, and "FeTnHex-2-Pyp4+" refers to the iron analog of MnTnHex-2-PyP5+.

EXAMPLES 2-3

Topical Administration

The efficacy of Manganese ortho tetrakis(N-n-butoxyethylpyridinium-2-yl)porphyrin (MnTriBuOE-2-PyP$^{5+}$) in treating pruritus (itch) when topically applied was evaluated in a 38 year old caucasian male with large areas of moderately severe plaque-forming psoriasis on upper and lower portions of both legs, with each involved area being approximately 10-20 cm in diameter. These lesions were markedly excoriated with intense, persistent symptoms of pruritus. MnTnBuOE-2-PyP$^{5+}$ was formulated in Lipoderm at 0.01% and 0.1% concentrations producing a light brown cream which was applied bid. to lesions on one extremity. Symptoms of pruritus were relieved within 10 to 15 minutes after topical application of MnTriBuOE-2-PyP$^{5+}$ and remained under control for several hours. Repeat application of MnTnBuOE-2-PyP$^{5+}$ consistently reduced pruritus without tachyphylaxis. Equivalent efficacy was achieved for lesions treated with both 0.01% and 0.1% MnTnBuOE-2-PyP$^{5+}$ in Lipoderm.

A second subject, a 70 year old caucasian male, with psoriatic involvement of the scalp of moderate severity and associated with marked pruritus and scratching was topically treated with MnTnBuOE-2-PyP$^{5+}$ 0.1% in Lipoderm twice daily for 3 weeks. Symptoms of pruritus were relieved within minutes after application of MnTnBuOE-2-PyP$^{5+}$ and remained under control for up to 12 hours. Treatment with the drug twice daily was completely effective in resolving pruritic symptoms, The foregoing is illustrative of the present invention, and is not to be construed as limiting thereof. The invention is defined by the following claims, with equivalents of the claims to be included therein.

That which is claimed is:

1. A method of treating pruritus in skin of a subject in need thereof, comprising administering to said subject an active agent in a treatment effective amount to treat pruritus in said skin of said subject,
   wherein said administering comprises topically administering to said skin of said subject a composition comprising said active agent in an amount of 0.01% to 1% by weight of said composition, and
   wherein said active agent is a compound having a structure represented by:

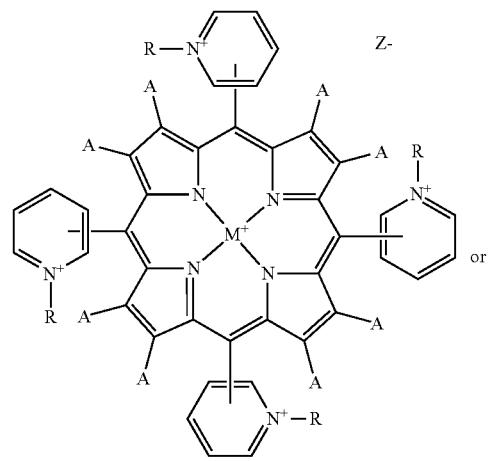

wherein:
    each R is independently $C_{1-12}$ alkyl or —$(CH_2)_mCH_2OX$;
    m is 1 or 2;
    X is $C_{1-12}$ alkyl;
    each A is an independently selected hydrogen, halogen, —$NO_2$, or —CHO;
    M is manganese, iron, copper, cobalt, nickel or zinc; and
    $Z^-$ is a counterion;
or a pharmaceutically acceptable salt thereof.

2. The method of claim 1, wherein said subject is afflicted with dermal or pruritoceptive itch.

3. The method of claim 1, wherein said subject is afflicted with neuropathic itch.

4. The method of claim 1, wherein said subject is afflicted with neurogenic itch.

5. The method of claim 1, wherein said subject is afflicted with psychogenic itch.

6. The method of claim 1, wherein said active agent has a structure represented by:

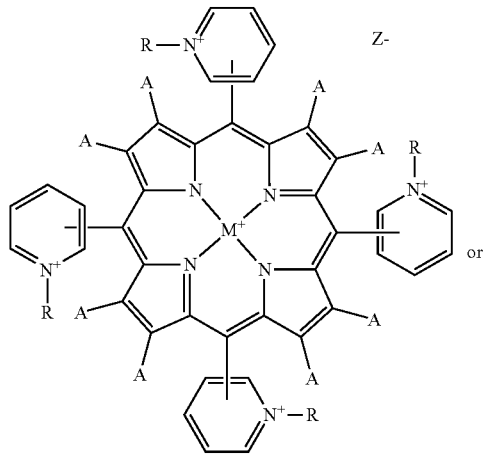

wherein:
each R is $C_{1-12}$ alkyl;
each A is, independently, hydrogen, halogen, —NO$_2$ or —CHO;
M is metal selected from the group consisting of manganese, iron, copper, cobalt, nickel and zinc, and
$Z^-$ is a counterion.

7. The method of claim 1, wherein said active agent has the structure:

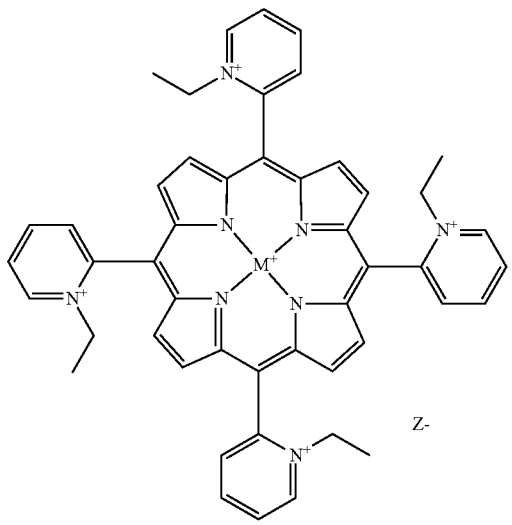

wherein $Z^-$ is a counterion.

8. The method of claim 1, wherein said active agent has a structure represented by:

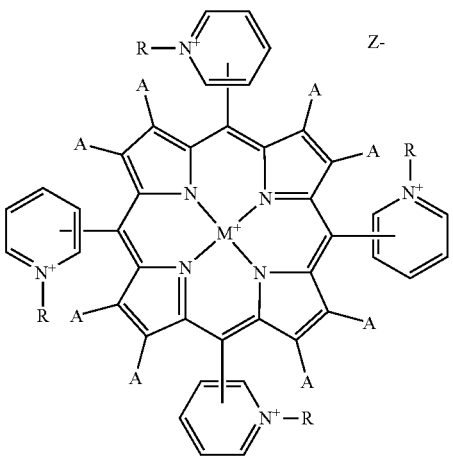

wherein:
each R is —(CH$_2$)$_m$CH$_2$OX;
m is 1 or 2;
X is $C_{1-12}$ alkyl;
each A is, independently, hydrogen, halogen, —NO$_2$ or —CHO;
M is metal selected from the group consisting of manganese, iron, copper, cobalt, nickel and zinc, and
$Z^-$ is a counterion.

9. The method of claim 1, wherein said active agent has the structure:

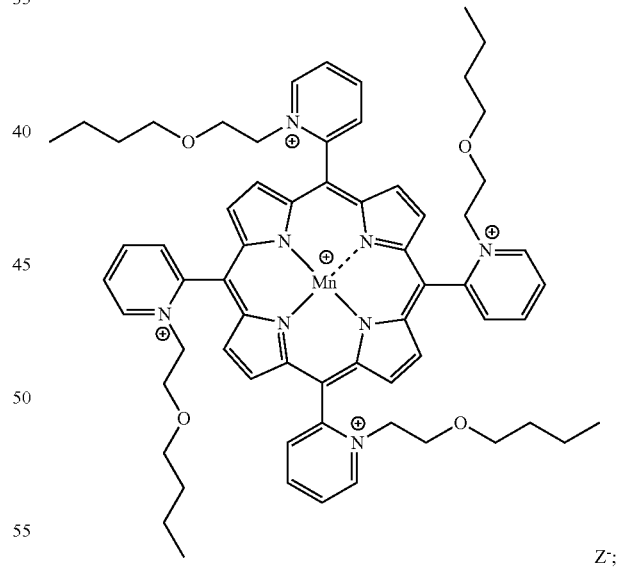

wherein $Z^-$ is a counterion.

10. The method of claim 1, wherein said composition comprises said active agent in an amount of 0.01% to 0.1% by weight of said composition.

11. The method of claim 1, wherein said administering relieves pruritus in said skin of said subject within 30 minutes of administering said active agent to said skin.

12. The method of claim 1, wherein said administering reduces frequency of scratching a region of said skin within 30 minutes of administering said active agent to said skin.

13. The method of claim 1, wherein said administering reduces urge to scratch a region of said skin within 30 minutes of administering said active agent to said skin.

14. The method of claim 1, wherein said administering relieves pruritus in said skin of said subject within 15 minutes of administering said active agent to said skin.

15. The method of claim 1, wherein said administering relieves pruritus in said skin of said subject for up to 12 hours after administering said active agent to said skin.

* * * * *

UNITED STATES PATENT AND TRADEMARK OFFICE
CERTIFICATE OF CORRECTION

PATENT NO. : 10,080,759 B2
APPLICATION NO. : 15/109164
DATED : September 25, 2018
INVENTOR(S) : Ji et al.

Page 1 of 1

It is certified that error appears in the above-identified patent and that said Letters Patent is hereby corrected as shown below:

On the Title Page

Item (72) Inventors: Please correct "Grenwood Village, CO" to read -- Greenwood Village, CO --

In the Specification

Column 2, Line 3: Please correct "MnInHex-2-PyP5+" to read -- MnTnHex-2-PyP5+ --

Column 7, Line 31: Please delete the word "or" on the right of formula A2

Column 8, Line 30: Please delete the word "or" on the right of formula B2

Column 9, Line 56: Please delete the word "or" on the right of formula C2

Column 19, Line 58: Please correct "(MnTriBuOE-2-PyP$^{5+}$)" to read -- (MnTnBuOE-2-PyP$^{5+}$) --

Column 20, Line 3: Please correct "MnTriBuOE-2-PyP$^{5+}$" to read -- MnTnBuOE-2-PyP$^{5+}$ --

Column 20, Line 19: Please correct "symptoms," to read -- symptoms. --

In the Claims

Column 21, Claim 6, Line 24: Please delete the word "or" on the right of the formula Signed and Sealed this
Fifteenth Day of January, 2019

Andrei Iancu
*Director of the United States Patent and Trademark Office*